United States Patent [19]
Burk et al.

[11] 4,111,988
[45] Sep. 5, 1978

[54] 4-(2,2-DICHLORO-1,1-DIFLUOROETHOXY-BENZENE) SULFONYL CHLORIDE AND ITS PREPARATION

[75] Inventors: George A. Burk, Bay City; Christian T. Goralski; Craig E. Mixan, both of Midland, all of Mich.

[73] Assignee: The Dow Chemical Company, Midland, Mich.

[21] Appl. No.: 758,283

[22] Filed: Jan. 10, 1977

[51] Int. Cl.$^2$ ............................................. C07C 143/70
[52] U.S. Cl. ............................ 260/543 R; 260/465 F; 424/304
[58] Field of Search ..................................... 260/543 R

[56] References Cited
U.S. PATENT DOCUMENTS

| 2,866,821 | 12/1958 | Wargotz et al. | 260/543 R |
| 3,578,710 | 5/1971 | Bruson et al. | 260/543 R |
| 3,772,373 | 11/1973 | Lee | 260/543 R |
| 3,878,242 | 4/1975 | Hempel et al. | 260/543 R |

FOREIGN PATENT DOCUMENTS 163,888 11/1933 Switzerland ........................ 260/543 R

OTHER PUBLICATIONS

England et al., "J.A.C.S.," vol. 82, p. 5116, (1960).
Park et al., "J.A.C.S.," vol. 70, p. 1550, (1948).
"Canadian Jour. of Chem.," (43)6, p. 1870–1874, (1965).

Primary Examiner—Norman Morgenstern
Attorney, Agent, or Firm—Theodore Post; Daniel L. DeJoseph; C. Kenneth Bjork

[57] ABSTRACT

The compound of this invention is prepared by reacting phenol as such or as its alkali metal phenate with dichlorodifluoroethylene to form 2,2-dichloro-1,1-difluoroethoxybenzene and reacting the latter with chlorosulfonic acid and recovering the reaction product. The compound of this invention, when reacted with acrylonitrile gives the antimicrobial compound, 2-chloro-3-(4-(2,2-dichloro-1,1-difluoroethoxy)phenyl)-sulfonyl)propanenitrile.

2 Claims, No Drawings

4-(2,2-DICHLORO-1,1-DIFLUOROETHOXYBENZENE) SULFONYL CHLORIDE AND ITS PREPARATION

BACKGROUND OF THE INVENTION

No art is known for the compound of this invention and its preparation.

SUMMARY OF THE INVENTION 4-(2,2-Dichloro-1,1-difluoroethoxybenzene)sulfonyl chloride, hereinafter referred to as "Compound" is prepared in a two-step process, as represented by the following schematic equations:

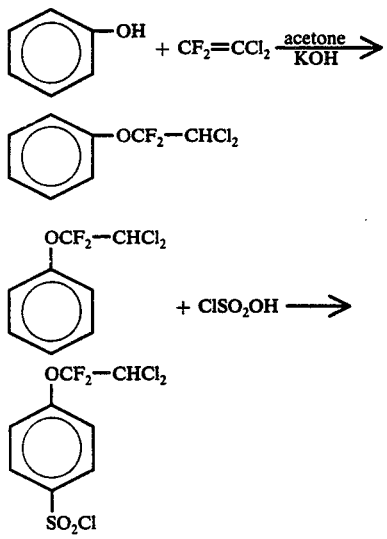

In the first step, phenol (94 g, 1 mole) is dissolved in acetone, cooled to about 10° C. and powdered KOH (11 g, 85%, 0.17 mole) is added thereto with mixing. NaOH may be substituted for KOH, if desired. After solution, dichlorodifluoroethylene is gradually introduced into the reaction mixture which is maintained at about 10°--12° C. The resulting exothermic reaction is controlled by substituting a Dry Ice ® bath in place of the ice water bath to cool down the reaction mixture to about 10° C. in a short time period. In the reaction mixture, phenol as such and as alkali metal phenate is present in excess. After completion of the reaction, the reaction mixture is poured over ice, stirred, allowed to settle, and the oily layer containing the reaction product is separated therefrom. It is washed with bicarbonate of soda solution and with water to remove excess phenol and phenate, and a nearly colorless organic layer (183 g, 81% yield) is thereafter separated. The crude 2,2-dichloro-1,1-fluoroethoxybenzene is thereafter distilled, 87% being recovered as a center cut.

In the second step, 22.7 g, 0.1 mole of the last-named product is gradually added with stirring to a large excess of chlorosulfonic acid cooled to 0° to 10° C. The reaction mixture is continuously stirred and allowed to warm up to room temperature. The reaction mixture is poured over ice and a viscous liquor is separated. The latter is dissolved in methylene chloride and the aqueous layer is extracted with the same. The methylene chloride extracts are combined, dried over anhydrous magnesium sulfate, filtered and the solvent is evaporated in vacuo to give Compound as a light amber liquid. Yield 24.5 g, 75%.

The structure of Compound is confirmed by nuclear magnetic resonance and infrared spectra.

Compound, when reacted with acrylonitrile, as described in our copending U.S. Pat. application Ser. No. 758,281, entitled "2-CHLORO-3-((4-(2,2-DICHLORO-1,1-DIFLUOROETHOXYPHENYL)SULFONYL)-PROPANENITRILE", filed simultaneously herewith, now U.S. Pat. No. 4,049,696, gives the antimicrobial product, 2-chloro-3-((4-(2,2-dichloro-1,1-difluoroethoxy)phenyl)sulfonyl)propanenitrile. The antimicrobial utility of the latter is shown in the referenced copending application.

What is claimed is:

1. 4-(2,2-Dichloro-1,1-difluoroethoxybenzene)sulfonyl chloride.

2. The method of making 4-(2,2-dichloro-1,1-difluoroethoxybenzene)sulfonyl chloride by mixing together at about 10° C., an excess of phenol as such or as its alkali metal phenate with dichlorodifluoroethylene in the presence of a solvent, recovering the resulting 2,2-dichloro-1,1-difluoroethoxybenzene from the reaction medium and mixing it with excess chlorosulfonic acid at a reaction temperature between about 0° C. and about room temperature and recovering 4-(2,2-dichloro-1,1-difluoroethoxybenzene)sulfonyl chloride from the reaction medium.

* * * * *

UNITED STATES PATENT AND TRADEMARK OFFICE
CERTIFICATE OF CORRECTION

PATENT NO. : 4,111,988
DATED : September 5, 1978
INVENTOR(S) : George A. Burk, et al.

It is certified that error appears in the above-identified patent and that said Letters Patent are hereby corrected as shown below:

Column 2, line 7, "1-fluoroethoxybenzene" should read -- 1-difluoroethoxybenzene --.

Signed and Sealed this

First Day of May 1979

[SEAL]

Attest:

RUTH C. MASON
Attesting Officer

DONALD W. BANNER
Commissioner of Patents and Trademarks